(12) United States Patent
Firon et al.

(10) Patent No.: US 7,624,621 B2
(45) Date of Patent: Dec. 1, 2009

(54) METHOD AND DEVICE FOR MEASUREMENT OF PERMEATION

(75) Inventors: Muriel Firon, Egly (FR); Stéphane Cros, Chambery (FR); Philippe Trouslard, Chevreuse (FR)

(73) Assignee: Commissariat A l'Energie Atomique (FR)

( * ) Notice: Subject to any disclaimer, the term of this patent is extended or adjusted under 35 U.S.C. 154(b) by 177 days.

(21) Appl. No.: 11/402,230

(22) Filed: Apr. 11, 2006

(65) Prior Publication Data

US 2007/0186622 A1 Aug. 16, 2007

(30) Foreign Application Priority Data

Feb. 15, 2006 (FR) .................................. 06 01320

(51) Int. Cl.
*G01N 15/08* (2006.01)
(52) U.S. Cl. ........................................................ 73/38
(58) Field of Classification Search ................ 73/38, 73/37
See application file for complete search history.

(56) References Cited

U.S. PATENT DOCUMENTS

| | | | |
|---|---|---|---|
| 5,131,261 A | 7/1992 | Tou et al. | |
| 5,138,870 A * | 8/1992 | Lyssy | ............................. 73/38 |
| 5,265,463 A | 11/1993 | Loebig | |
| 6,804,989 B2 | 10/2004 | Bujas et al. | |
| 6,964,191 B1 * | 11/2005 | Tata | ............................. 73/38 |
| 7,094,036 B2 * | 8/2006 | Mennie et al. | ................. 417/53 |
| 7,121,135 B2 * | 10/2006 | Moore | ............................ 73/38 |
| 2003/0001086 A1 | 1/2003 | Noerenberg et al. | |
| 2004/0083796 A1 * | 5/2004 | Bujas et al. | ..................... 73/38 |
| 2004/0123646 A1 * | 7/2004 | Echigo et al. | ................... 73/38 |

FOREIGN PATENT DOCUMENTS

JP 63-061141 3/1988

(Continued)

OTHER PUBLICATIONS

Ranade et al.; "High sensitivity gas permeable measurement system for thin plastic films", Review of Scientific Instruments, vol. 76, 013902, 2005 American Institute of Physics.

(Continued)

*Primary Examiner*—Hezron Williams
*Assistant Examiner*—Gunnar J Gissel
(74) *Attorney, Agent, or Firm*—Lerner, David, Littenberg, Krumholz & Mentlik, LLP

(57) ABSTRACT

The invention relates to a method for measuring gases permeation through a material (M), comprising the steps of:
Forming a mixture of isotopic gases in a mixing enclosure (14), each isotopic gas corresponding to a target gas for which permeation through the material (M) is sought, the isotopic gas having a mass number different from that of the corresponding target gas;
Filling with the mixture of isotopic gases a first chamber (11) of a permeation enclosure (10) comprising first (11) and second (12) chambers, the first chamber (11) being separated from the second chamber (12) by the material (M);
Simultaneously analyzing the isotopic gases having permeated through the material (M) and being present in the second chamber (12), in order to simultaneously calculate permeation through the material (M) of each of the corresponding target gases.

The invention further relates to a device for implementing such a method, and a method for using this device.

34 Claims, 2 Drawing Sheets

FOREIGN PATENT DOCUMENTS

| | | | |
|---|---|---|---|
| JP | 63061141 A | * | 3/1988 |
| WO | WO-02/088657 | | 11/2002 |

OTHER PUBLICATIONS

Mocon Brochure, "Modular Carbon Dioxide Transmission Rate Test System for Barrier Films, Packages, and Bottles", Copyright 1997, Modern Controls, Inc.

Mocon Brochure, "Permatran-W Model 3/33, The Standard for Water Vapor Transmission Rate Testing of Flat Films & Finished Packages", Copyright 2002, MOCON, Inc.

Mocon Brochure, "OX-TRAN Model 2/21, The Standard for Oxygen Transmission Rate Testing of Flat Films & Finished Packages", 2002 MOCON Inc.

* cited by examiner

METHOD AND DEVICE FOR MEASUREMENT OF PERMEATION

FIELD OF THE INVENTION

This invention relates to the field of gas permeation, and more particularly to a device and a method for measuring gas permeation through solid materials.

TECHNICAL BACKGROUND

Selection of materials for some applications, such as packaging or electronics for example, requires studying permeation of some gases through these materials. Permeation refers to the mechanism by which a gas passes through a material in several steps, namely absorption of the gas in the material, diffusion of this gas through the material, and desorption of the gas on the other side of the material. The most commonly used permeation measurements generally concern to gases such as oxygen or water vapour through materials to be selected.

For example for materials intended to be used for agri-food packaging, it is critical to study permeation of common gases, and particularly oxygen and water vapour, through the materials. The required permeability levels to these gases are extremely low, and consequently the permeation study requires permeation measurement devices with high sensitivities.

Many permeation measurement devices have been developed in response to this problem, based on various gas monitoring principles, each with their disadvantages.

In particular, a device has been developed for measuring permeation flows of $O_2$, Ar or He, comprising a measurement enclosure in ultra vacuum. However, the sensitivity of this measurement method is limited by the residual pollution level of the monitored gas in the vacuum measurement enclosure, oxygen and water vapour present in the atmosphere naturally being among the greatest pollutants, even in a vacuum enclosure.

To overcome this severe disadvantage, it has been proposed to use an isotope of the target gas for which it is required to determine permeation through the material, using in other words a gas corresponding to the target gas but with a different mass number. Thus, by using a mass spectrometer as an analyser in the measurement enclosure for example, the permeation detection thresholds can be reduced by several orders of magnitude. Since the natural isotopic abundance of these elements is very low, pollution of the enclosure by these species becomes less important.

This measurement method increases the sensitivity of permeation measurements. Nevertheless, measurement times for target gases such as water vapour or oxygen are not at all lower than with conventional methods. These methods can measure the permeability of only one target gas through a film. Since the films and particularly films with a thin coating) are very fragile, any manipulation could cause an alteration to the film barrier properties (for example due to a scratch). If a change of the target gas requires modification of the instrumental device, it will often be necessary to replace the film for each measurement, which creates a lack of reproducibility and reliability of the measurements.

It is therefore a goal of the invention to propose improved device and method for measuring permeation, which in particular combine sensitivity and shorter measurement times.

SUMMARY OF THE INVENTION

To this end, the invention relates to a method for measuring gases permeation through a material, comprising the steps of:

Forming a mixture of isotopic gases in a mixing enclosure, each isotopic gas corresponding to a target gas for which permeation through the material is sought, the isotopic gas having a mass number different from that of the corresponding target gas;

Filling with the mixture of isotopic gases a first chamber of a permeation enclosure comprising first and second chambers, the first chamber being separated from the second chamber by the material;

Simultaneously analysing the isotopic gases having permeated through the material and being present in the second chamber, in order to simultaneously calculate permeation through the material of each of the corresponding target gases.

The preliminary formation of a mixture of gases in the mixing enclosure enables filling the first chamber with a mixture that might comprise several isotopic gases, each corresponding to one target gas for which permeation through the material is to be studied. Thus, all isotopic gases of the mixture will permeate through the material and the analysis means will therefore be further capable of simultaneously analysing the gases that permeated through it.

The first advantage of this simultaneous analysis lies in the measurement times that are shorter when there are more gases to be analysed. The importance of this advantage becomes obvious when considering, for example, that a measurement of the permeation of $O_2$ through a material can take several days or even several months, depending on the permeability of the material.

Further, the fact that measurements are made simultaneously may demonstrate, if any, an interdependence between adsorption of water vapour by a film and the permeability of this film to one or several other gases. Adsorption of water vapour may namely modify the diffusion properties of another gas, for example oxygen, through a film. Simultaneous measurements of permeation of water vapour and oxygen are made, instead of simply fixing the moisture content during oxygen permeation measurements.

Moreover, experimental conditions under which the measurements are made (particularly in terms of temperature, degradation of the material, etc.) are identical for each gas as the analyses are made in parallel, and therefore the permeation analyses for a particular material become much more reliable.

Preferred but non-limitative aspects of the method according to the invention are as follows:

the step of forming a mixture of isotopic gases consists in filling the mixing enclosure with at least one isotopic gas originating from a gas source, closing the mixing enclosure, regulating heavy water vapour in the mixture using a phase regulation means, and waiting for the mixture to reach equilibrium;

the mixing enclosure is filled with an isotopic gas chosen from among $^{18}O_2$ and $^{17}O_2$ when one of the target gases is $^{16}O_2$;

the step of filling the first chamber consists in creating a vacuum in the first chamber with a first pumping means, then opening the mixing enclosure to fill the first chamber with the mixture of isotopic gases;

the method further comprises a step of thermal regulation prior to the analysis step, the thermal regulation step consisting in regulating the temperature of the permeation enclosure and the mixing enclosure with a temperature regulation means;

the analysis step consists in simultaneously determining the presence of isotopic gases in the second chamber with a gas analyser located in a measurement enclosure, the measurement enclosure being connected to the second chamber and kept under a continuous vacuum using a second pumping means;

the method further comprises a step prior to the analysis step consisting in creating a vacuum in the second chamber and the measurement enclosure using the second pumping means;

the method further includes a gas recovery step, consisting in recovering the mixture of isotopic gases from the first chamber once the permeation analysis has been finished, and transferring the mixture to a filter means in order to dry gases of the mixture;

the gas recovery step further includes a step consisting in trapping dried gases from the mixture in the corresponding gas source with a recovery means adapted for recovering the corresponding gas;

the method further includes a preliminary test step consisting in filling the first chamber with helium and calculating helium permeation through the material, in order to preselect the material by excluding the material from subsequent analyses if helium permeation through the material is greater than a determined threshold.

The invention also relates to a device for measuring gas permeation through a material, comprising:

a permeation enclosure comprising a first chamber and a second chamber separated by the material, a gas analysis means for analysis of the gases having permeated through the material and being present in the second chamber, and a mixing enclosure for forming a mixture of isotopic gases, each isotopic gas corresponding to a target gas for which permeation through the material is sought, the isotopic gas having a mass number different from that of the corresponding target gas, the mixing enclosure being connected to the first chamber to fill the first chamber with the mixture of isotopic gases, such that the analysis, means simultaneously calculates permeation through the material of each of the corresponding target gases.

The following are preferred but non-limitative aspects of the device according to the invention:

the device further comprises a gas supply line including first and second ends, the first end being connected to at least one isotopic gas source, and the second end being connected to the first chamber and the mixing enclosure in order to fill the first chamber and/or the mixing enclosure;

the supply line is connected to the mixing enclosure, to the first chamber, and to the gas source through a first valve, a second valve, and a third valve respectively;

the gas source is further connected to a recovery means adapted for recovering the corresponding gas, wherein the recovery means may be a cryogenic trap;

the supply line is further connected to a filter means for drying gases circulating in the supply line;

the filter means is a molecular sieve adapted to trap water molecules in gases circulating in the supply line;

the filter means includes an inlet and an outlet, the inlet and the outlet being connected to the supply line through a fourth valve and a fifth valve respectively, the supply line further including a sixth valve located between the fourth valve and the fifth valve to bypass the supply line;

the supply line further includes a seventh valve inserted at the second end before the first and second valves, in order to isolate the supply line from the mixing enclosure and from the first chamber of the permeation enclosure;

the supply line is further connected to a first pumping means through a ninth valve at the first end, in order to create a vacuum in the supply line;

the mixing enclosure is further connected to a phase regulation means for regulating the phase of the species in the mixing enclosure;

the phase regulation means is a Peltier effect module regulating the temperature of a saline solution saturated in heavy water;

the device further comprises a temperature regulation means for regulating the temperature of the permeation enclosure and the mixing enclosure;

the analysis means comprises an analyser located in a measurement enclosure comprising first and second ends, the first end being connected to the second chamber, and the second end being connected to a second pumping means to create a vacuum in the measurement enclosure;

the first end of the measurement enclosure is connected to the second chamber through a tenth valve;

the second pumping means comprises a primary pump and a secondary pump arranged in series;

the analyser is a mass spectrometer, the mass spectrometer being positioned within the gas flow path between the second chamber and the pumps.

Finally, the invention relates to a method for using the permeation measurement device, wherein the method comprises the steps of:

Setting up a sample film of a material to be measured in the permeation enclosure, and closing all valves of the device;

Opening the tenth valve and the eleventh valve and creating a vacuum in the second chamber using the second pumping means;

Arranging the saline solution saturated in heavy water within the mixing enclosure and freezing the solution using the Peltier effect module;

Opening the first, second, fourth, fifth, sixth, seventh and ninth valves and creating a vacuum in the first chamber, the supply line, the mixing enclosure and the filter means using the first pumping means;

Closing the second, fourth, fifth and ninth valves;

Opening the third valve to fill the mixing enclosure with an isotopic gas from the isotopic gas source;

Closing the first valve and recovering the isotopic gas from the supply line using the recovery means;

Closing the third, sixth and seventh valves and waiting for the mixture to reach equilibrium;

Opening the first and second valves and simultaneously calculating permeation through the material of each target gas using the analysis means.

This method of use may also include the following steps:

Freezing the saline solution using the Peltier effect module;

Closing the sixth valve and opening the third, fourth, fifth and seventh valves, and drying the gases with the filter means;

Recovering dried gases using the recovery means, and closing the third valve.

BRIEF DESCRIPTION OF THE DRAWINGS

Other characteristics and special features of the invention will become clearer from the following non-limitative description given for illustrative purposes only, and should be read with reference to the appended figures, wherein.

DETAILED DESCRIPTION OF THE DRAWINGS

The permeation of a gas through a material M depends on differences between the partial pressures of this gas, also called permeant, on each side of the material M, generally sampled in the form of a film F.

Figure 1:
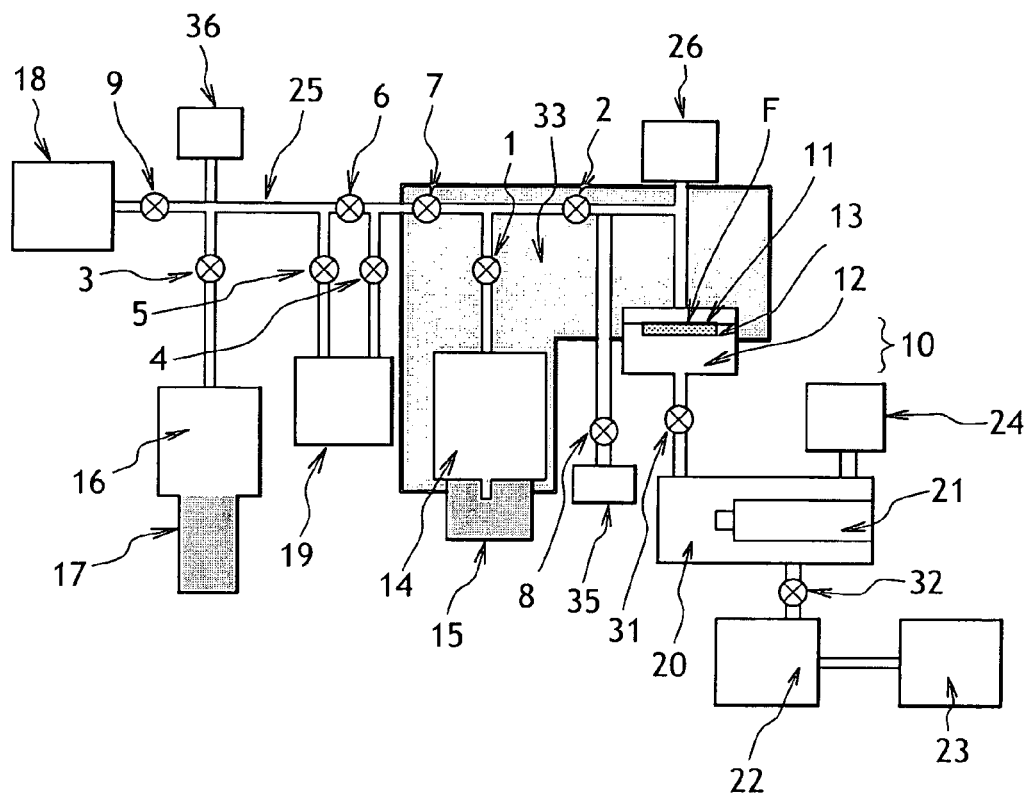
FIG. 1 is a schematic diagram illustrating the permeation measurement device according to the invention.

The permeameter, for which the block diagram is illustrated in FIG. 1, comprises a permeation enclosure 10 that comprises a first chamber 11 and a second chamber 12 separated by the film F of material M. When studying differences in the partial pressures of the permeant between the first chamber 11 on the upstream side in the device and the second chamber 12 on the downstream side in the device, it is important to maintain a downstream partial pressure to be zero, or negligible compared with the upstream pressure. A controlled atmosphere with a determined upstream pressure of the permeant(s) is made above the film to be tested. Below the film, the second chamber 12, in which a high vacuum is maintained, enables to keep the downstream pressure equal to zero, or negligible compared with the upstream pressure.

In order to prevent excessive deformation of the film F, the permeation enclosure 10 contains a support means 13, such as a porous sintered metallic material. The film F thus lies on this support means 13, which is located between the first chamber 11 and the second chamber 12, and which is formed so as to enable transmission of gases.

Figure 2:
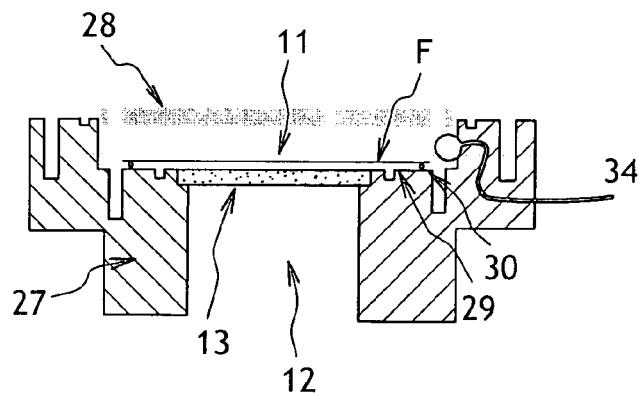
FIG. 2 is a sectional view of the fixation mechanism of a film in the permeation device according to the invention.
Figure 3:
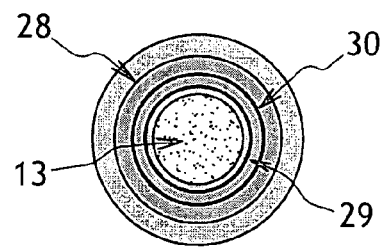
FIG. 3 is a top view of the mechanism of FIG. 2.

FIGS. 2 and 3 illustrate a fastening mechanism that may be provided inside the permeation enclosure 10 to fix a sample film F in the permeation enclosure 10.

The fixation mechanism comprises a frame 27 having a substantially symmetry of revolution and with a through-opening along the axis of revolution. The frame 27 is shaped to hold the sintered metallic material 13 for separating the first chamber 11 from the second chamber 12. For example, the sintered metallic material 13 may be in the form of a disk, this disk being supported by a cranked part provided on the internal periphery of the frame 27. The sample film F of material M is then placed on this sintered metallic material 13. For example, it would be possible to have a sample disk with a surface area larger than the surface area of the sintered metallic material 13, in order to entirely cover the sintered metallic material 13. In practice, the size of the sample film. F is of the order of 12 cm².

Furthermore, seals are provided between the sintered metallic material 13 and the sample film F around the periphery of the sample film F, to obtain a perfect seal between the first chamber 11 and the second chamber 12. A clamping ring 28 bears in contact with the film F to compress the seals, and to make the joint between the first chamber 11 and the second chamber 12 leak tight. For example, an O-ring 29 and an indium seal 30 could be used.

An analysis means is connected to the second chamber 12 on the downstream side of the film F, this analysis means being adapted to monitor the downstream partial pressure of the permeant(s). The analysis means of the measurement device comprises a measurement enclosure 20 connected to the second chamber 12 through a valve 31 that can isolate the measurement enclosure 20 from the second chamber 12 if necessary. A vacuum is created in this measurement enclosure 20 by a pumping system comprising a primary pump 23 (i.e. a vacuum pump) and a secondary pump 22 (i.e. a high vacuum pump), which are preferably placed in series with each other. The measurement enclosure and the pumping system are connected through a valve 32.

Further, the analysis means comprises a residual gas analyser 21 located in the measurement enclosure 20 under a vacuum, and arranged so as to analyse the gases from the second chamber 12 with the best sensitivity, before they are pumped in by the pumps 22 and 23. For example, the analyser 21 could be a mass spectrometer placed within a measurement enclosure 20 in which a vacuum is created by a dry vacuum pump 23 and a turbopump 22 placed in series. For better sensitivity, the spectrometer is placed within the path of the gas flow between the second chamber 12 and the pumps 22 and 23. A pressure sensor 24 could also be provided to measure the total pressure inside the measurement enclosure 20.

The mass spectrometer 21 that is used can only operate at low pressures, and therefore requires a measurement enclosure 20 under a secondary vacuum (of the order of $10^{-4}$ torr maximum). Consequently, the measurement enclosure 20 is permanently pumped with the pumps 22 and 23 during the transfer of gases by permeation through the sample film F. Thus, the partial pressure of each of the gases that permeated through the sample increases until it becomes stable when the permeation flow becomes equal to the pumped flow. The mass spectrometer 21 outputs a signal that is a current resulting from ionisation of atoms of a measured species, and is proportional to the partial pressure in this species. Since pumping is efficient and permeation through the samples is low, the stabilisation pressure is also very low such that it can be considered that the pressure on the downstream face of the sample film F remains practically zero over time. The flow of a permeant through the sample film F is therefore proportional to the partial pressure of the monitored permeant when the steady state is achieved. For extremely low permeation flows, closing the valve 32 enables a cumulative measurement within the limit of the total pressure fixed by the analysis means 21, namely of the order of $-10^{-4}$ torr which makes it possible to respect the criterion that the downstream pressure should be negligible compared with the upstream pressure.

Starting from the permeation flow thus calculated, the permeability of the material M to the gas considered can be deduced by considering the thickness e of the sample film F.

Furthermore, the diffusion coefficient can be determined by examining the cumulated permeation flows over the entire experiment, using the known "time-lag" method. This method consists in tracing the cumulated permeation flows of a gas as a function of time, and making an extrapolation of the linear regression with zero cumulation starting from values corresponding to the steady state. The time $T_L$ obtained is directly related to the diffusion coefficient D by the following formula:

$$D = \frac{e^2}{6 \cdot T_L}$$

The sensitivity of the measurements is determined by the residual pollution level of the mass monitored by spectrometry in the measurement enclosure 20 under a vacuum. Water $H_2O$ and oxygen $O_2$, with mass numbers equal to 18 and 32 respectively, are naturally among the most important pollutants, but are the most important species for the study of permeation through a material M. This problem of residual pollution for water and for oxygen and also for other gases to be studied is overcome by making measurements using isotopic gases, for example such as deuterium ($D_2O$) for water vapour with a mass number equal to 20, and oxygen 18 ($^{18}O_2$) for oxygen with a mass number equal to 36.

As mentioned above, in order to determine the permeability of a material M to a particular gas, it is necessary to reach a steady state during the analysis. However a very long time may be necessary before reaching this steady state for gases such as water vapour and oxygen, if the barrier properties of the material M are good. Thus, several weeks may be necessary for complete characterisation of a material M in terms of permeation with regard to a set of considered gases and particularly permeation of oxygen and water vapour.

In a process for selection of a material M for subsequent use as a material for encapsulation for example, a solution could be to make a preselection of the material by measuring the permeation of helium He through the considered material. Indeed, Helium only interacts slightly with the material and has a small molecular radius, so that it is characterised by short diffusion times, which correspondingly reduces measurement times because the steady state is reached much more quickly, usually in a few minutes, or possibly a few hours for materials with the highest performance in terms of barrier properties. Even if permeation mechanisms of helium are significantly different from the permeation mechanisms of water vapour or oxygen, helium measurements very roughly define the barrier properties of the material and can be used to preselect materials for which measurements of permeation of water vapour and/or oxygen are necessary.

For example, if we are looking for materials with very low permeability to gases (as is the case for encapsulation in which acceptable flows of water vapour and oxygen are equal to $10^{-6}$ g/m$^2$.d and $10^{-3}$ g/m$^2$.d respectively), then there is no need to make complementary measurements if the permeability of the material to helium is high. Therefore, measuring the permeation of helium enables a preselection that may avoid the need to make subsequent measurements of the permeability of the material to water vapour and oxygen which are very long. Nevertheless, this solution has the disadvantage that it can only be applied during a material selection process, and cannot be used to reduce measurement times when the complete characterisation of the material is to be done, and particularly in terms of water and oxygen permeations. This selection process can be achieved using a gas reserve 35, that may be a helium cylinder fitted with a pressure reducing manometer, this gas reserve 35 being connected to the supply line 25 through a valve 8. Helium is injected into the gas supply line 25 directly through the reserve 35 after having opened valve 8 and closed valve 2. The injected pressure is measured using the pressure control means 26.

A complementary solution is to make permeation measurements of different gases simultaneously. To this end, an atmosphere containing a mixture of several isotopic gases has to be injected into the first chamber 11 of the permeation enclosure 10, and these gases will be able to permeate simultaneously through the material M to be studied. Nevertheless, the creation of such an atmosphere containing several different gases requires a particular gas supply means that will subsequently be described in detail.

The gas supply means used in the measurement device comprises a main gas supply line 25 through which a mixture of isotopic gases can be formed, this mixture of isotopic gases then being injected into the first chamber 11 of the permeation enclosure 10.

The gas supply line 25 namely comprises a first and a second end, the second end being connected to the first chamber 11 of the permeation enclosure 10 through a valve 2 that may be closed or opened depending on whether or not the first chamber 11 is to be isolated from the gas supply line 25.

A mixing enclosure 14 is also connected to this second end through a valve 1 so that isolation of the mixing enclosure 14 from the gas supply line 25 is possible. A mixture of isotopic gases will be formed in this mixing enclosure 14 before being injected into the first chamber 11.

A Peltier effect module 15 is further coupled to this mixing enclosure 14 to be able to form the mixture of isotopic gases. This Peltier effect module 15 is used as a phase regulation means for regulating the phase of species present in the mixing enclosure 14, which is useful particularly during the pumping steps necessary for creating the mixture. For obtaining a mixture of isotopic gases, it would for example be possible to use a saline solution of heavy water placed in a bucket inside the mixing enclosure 14, for measurement of water vapour permeation. Using a Peltier effect module 15 enables better control over the temperature of the saline solution of heavy water in the bucket and at the same time phase transformation (solid or liquid) of the heavy water. Moreover, the nature of the salt used in the saline solution makes it possible to obtain a wide range of moisture contents adapted to the desired mixture. This allows control of the upstream partial pressure of water vapour, which obviously influences permeation values of water vapour but also of other permeants for example such as oxygen, due to various effects on the material.

Independently of the phase regulation means 15, a temperature regulation means 33 may be coupled to the mixing enclosure 14 and to the permeation enclosure 10, so that the upstream assembly including the film F of material M can be controlled in temperature during the measurement, particularly to study permeation mechanisms as a function of the temperature. The temperature has namely a large influence on the barrier properties of the material. A temperature probe 34 will be placed as close as possible to the film F for this purpose.

The first end of the supply line 25 is connected to a gas source 16, which may for example be an isotopic gas source such as oxygen 17 ($^{17}O_2$) or oxygen 18 ($^{18}O_2$). This gas source 16 is connected to the first end of the gas supply line 25 through a valve 3 so that a gas can be injected into the supply line 25, and therefore into the mixing enclosure 14 or directly into the first chamber 11. The injected pressure will be controlled using the pressure measurement means 36.

This gas source 16 may be coupled to a recovery means 17 adapted to the gas considered in order to trap the corresponding gas present in the gas supply line 25. For example, a cold trap such as a cryogenic trap could be used.

Note that other gas sources (not shown) may be connected to the first end of the supply line 25. For example, sources for other gases for which permeation through the material M is to be determined directly could be provided, but any other isotopic or non-isotopic gas source could also be used to make the mixture that will be injected into the first chamber 11.

A pumping means 18 is also connected to the first end of the supply line 25 through a valve 9. This pumping means 18 can be used to create the vacuum in the gas supply line 25 when needed. For example, this will be necessary before the mixture of isotopic gases is injected into the first chamber 11, but also when it is required to analyse new materials M. The pumping means 18 may be a dry vacuum pump.

Finally, it is further possible to provide a filter means 19 on the supply line 25, this filter means 19 being designed to dry gases circulating in the supply line 25, particularly after measurements made on the material M. Thus, this filter means 19 comprises an inlet and an outlet connected to the supply line 25 through a valve 4 and a valve 5 respectively. A valve 6 is also arranged on the supply line 25 between the valve 4 and the valve 5 to bypass the gas supply line if necessary. For example, the filter means 19 may be a molecular sieve adapted to trap water molecules of gases circulating in the supply line 25.

The detailed description given below of a combined measurement of permeation of water vapour and oxygen through a material M to be analysed illustrates operation of the measurement device, and more particularly of the specific gas supply means that enables injection of a mixture of isotopic gases into the first chamber 11.

One step prior to the measurement and necessary for any analysis of a material M, consists in placing the sample film F of material M to be analysed in the permeation enclosure 10. The first step for doing this consists in closing all valves of the measurement device. The following step resides in placing the sample film F to be analysed on the sintered metallic part 13 and in fixing it in the permeation chamber 10 with the clamping ring 28 of the fixation mechanism. Once the sample film F has been fixed in the permeation enclosure 10, this enclosure can be closed.

A secondary vacuum then needs to be created on the downstream side of the sample film F using the primary pump 23 and the secondary pump 22 of the analysis means. When sample films F are replaced, the valve 31 can be closed to maintain the secondary vacuum in the enclosure 20 and limit its contamination. This system limits pollution of the analysis chamber even if a primary vacuum has to be recreated in the enclosure 20 before a primary vacuum is created in the chamber 12, so as to avoid overheating of the secondary pump. Thus, all that is necessary to create a primary vacuum (of the order of $10^{-3}$ torr) on the downstream side of the sample, film F is to stop the secondary pump 22 and open the valve 31. Once the primary vacuum has been reached in the enclosure 20 and the chamber 12, the secondary pump 22 can create a secondary vacuum of the order of $10^{-7}$ torr in the assembly formed by the enclosure 20 and the chamber 12.

While the secondary vacuum is thus created on the downstream side of the sample film F, the mixture of isotopic gases can be formed within the mixing enclosure 14 before it is injected into the first chamber 11 of the permeation enclosure 10. In our example, an atmosphere is created containing a mixture of heavy water vapour and oxygen 18 ($^{18}O_2$), so that permeation analyses of heavy water and oxygen 18 ($^{18}O_2$) can then be simultaneously made through the sample film F.

The first step consists in putting a saline solution saturated in heavy water in a bucket located in the mixing enclosure 14. This solution is then frozen using the Peltier effect module 15 coupled to the mixing enclosure 14. The valves 1, 2, 4, 5, 6, 7 and 9 are then opened and the dry vacuum pump 18 is started to create a vacuum in the gas supply line 25 but also in the mixing enclosure 14, the filter means 19 and the first chamber 11.

Valves 2, 4, 5 and 9 are then closed and valve 3 is opened in order to open the gas source, which in this case is a source of oxygen 18 ($^{18}O_2$), so as to fill the mixing enclosure 14 with a certain quantity of oxygen 18 ($^{18}O_2$). The injected pressure is controlled using the pressure measurement means 36.

Valve 1 is then closed and the cryogenic trap 17 coupled to the gas source 16 is activated to recover oxygen 18 ($^{18}O_2$) remaining in the supply line 25 and trap it in the source of oxygen 18 ($^{18}O_2$).

The valves 3, 6 and 7 are then closed and, after having thawed the bucket of water using the Peltier effect module 15, we wait for the mixture to reach equilibrium within the mixing enclosure 14. For a mixture of heavy water/oxygen 18 ($^{18}O_2$), equilibrium is reached in about 24 hours.

As soon as the mixture of isotopic gases is formed, and the mixing enclosure 14 and the permeation chamber 10 have been thermostated to the required temperature using the temperature regulation means 33, the measurements can begin. This is done by opening the valves 1 and 2 such that the mixture of the mixing enclosure 14 fills the first chamber 11 and that the permeation process through the sample film F begins. A pressure sensor 26 located in the first chamber 11 is used to control the total pressure of the mixture of isotopic gases in the first chamber 11.

The spectrometer 21 is used to make simultaneous measurements of the different permeation flows of heavy water and oxygen 18 ($^{18}O_2$).

As explained above, the permeation flow increases until it becomes stable, and once the steady state has been reached, the partial pressure of each of the monitored isotopic gases can be determined.

Figure 4:
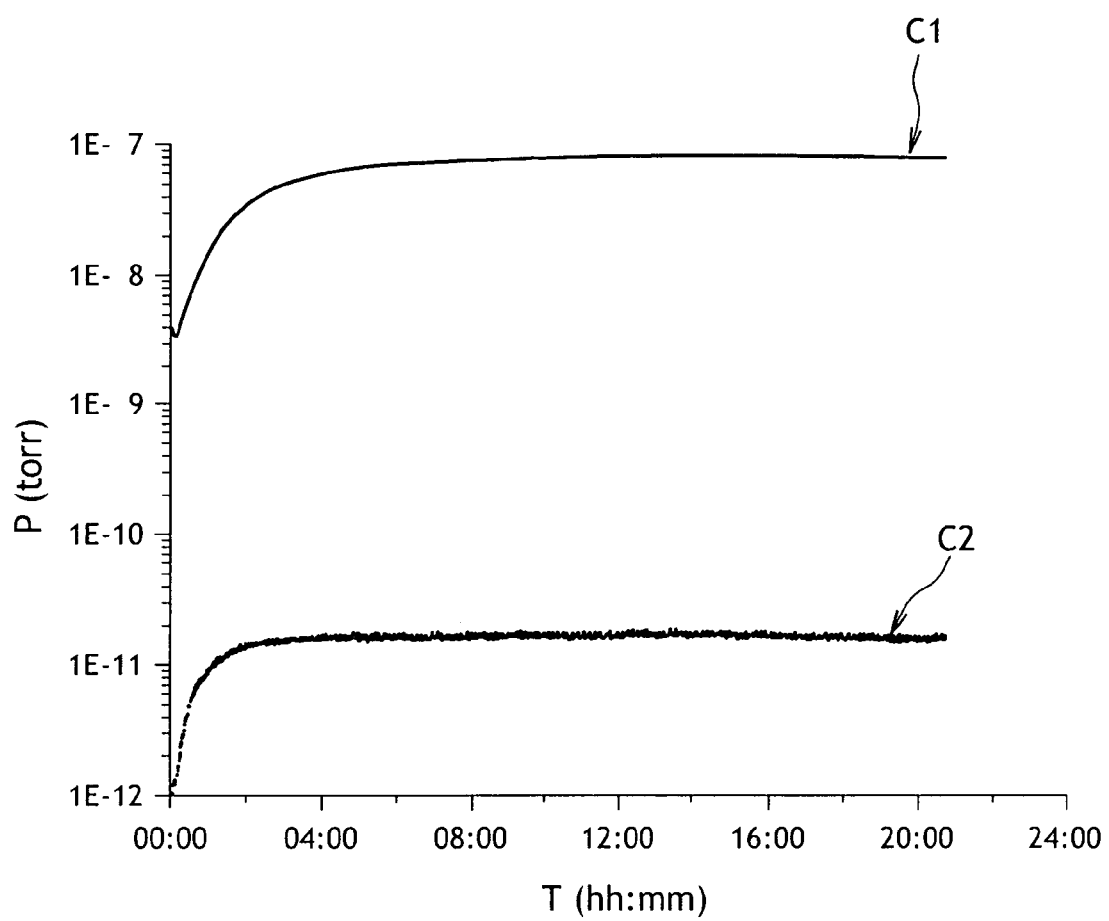
FIG. 4 shows curves illustrating an example of a combined measurement.

FIG. 4 presents an example of curves showing the variation of the partial pressure (in torr) of the heavy water (curve C1) and oxygen 18 ($^{18}O_2$) (curve C2) as a function of time (in hh:mm). These resulting curves are derived from a combined measurement of heavy water/oxygen 18 ($^{18}O_2$) on a film made from a polymer material coated with an inorganic layer under an atmosphere comprising a mixture of isotopic gases derived from a saturated saline solution of NaCl fixing a moisture content of 80% and a quantity of oxygen 18 ($^{18}O_2$) corresponding to a pressure of 700 torr. The assembly is thermostated to 23° C. (81° F.). The device had previously been calibrated with reference films with a known permeability.

Once the flows of heavy water and oxygen 18 ($^{18}O_2$) through the material M have stabilised, the mixture of isotopic gases should be purged from the first chamber 11. This can be done by providing any means of purging the first chamber 11, for example with a means for releasing the mixture of isotopic gases into the surrounding atmosphere.

Another solution that is preferred but not compulsory would be to recover the mixture of isotopic gases and isolate each of the gases that form this mixture. This recovery may be possible with the filter means 19.

Thus, the mixture of isotopic gases can be recovered by firstly freezing the solution within the mixing enclosure 14 using the Peltier effect module 15.

The valve 6 is then closed and the valves 3, 4, 5 and 7 are opened so as to make the mixture of isotopic gases pass through the filter means 19 which could for example be a molecular sieve designed to draw out water molecules present in the mixture.

When the gas mixture has been dried, all that remains in this particular example is oxygen 18 ($^{18}O_2$) that can be trapped in the gas source 16 using the cryogenic trap 17 provided for this purpose, before closing the valve 3.

This gas recovering process not only saves the gases that are used, but it also reduces pollution due to the release of gases into the environment.

Activation of the dry vacuum pump 18 also provides a means for completely purging the gas supply line 25, the filter means 19 and the first chamber 11.

As already mentioned, these combined heavy water/oxygen 18 ($^{18}O_2$) measurements may depend on a preliminary analysis of the permeation of helium through the sample film F of the material M to be analysed. If analyses of helium permeation through the material M show that the properties of the material M are not satisfactory, then it would be possible not to analyse the material in further detail, particularly concerning permeability of the material M to water and oxygen.

However, if the helium permeation measurements are satisfactory, the measurement device can be used to perform subsequent analyses on water and oxygen permeations through the same sample film F, without needing to modify the configuration of the measurement device.

It is namely only necessary to provide a helium source connected to the first end of the gas supply line 25 through a valve. This source enables to create a controlled helium atmosphere within the first chamber to measure helium permeation through the sample film F. The following step consists in recovering the helium remaining in the first chamber 11 after the helium permeation analysis and in purging the gas supply line 25 and the first chamber 11 using the dry vacuum pump 18. Then, if needed, the combined measurements of heavy water and oxygen 18 ($^{18}O_2$), and particularly the preliminary phase to form the mixture of isotopic gases can begin.

The above described device for measurement of permeation has the advantage to use smaller samples than commercial instruments and can be used to make all permeation measurements on a single sample film F, without creating excessive differences of the experimental conditions for successive permeation analyses.

The device further allows one to perform another analysis of permeation of helium through the same sample film F after the combined permeation analyses for heavy water and oxygen 18 ($^{18}O_2$), so as to be able to correlate the results and thus take account of structural changes that occur in the film F during the successive analyses.

Such method and device for simultaneous permeation measurements of isotopic gases through a material are particularly useful, for example when selecting materials for encapsulation of organic solar cells. The device enables measurements with high sensitivity of the order of $10^{-5}$ g/m$^2$ per day for water vapour. Obviously, use of the measurement method and device described is not restricted to encapsulation of organic solar cells and could be used for any application that requires measurements of flow densities with very low thresholds.

The invention claimed is:

1. A method for measuring gas permeation through a material comprising the steps of:
   a. forming a mixture of isotopic gases in a mixing enclosure, each of said isotopic gases corresponding to a different target gas for which permeation through said material is sought, each of said isotopic gases having a mass number different from that of said corresponding target gas;
   b. filling a first chamber of a permeation enclosure with said mixture of isotopic gases, said permeation enclosure comprising said first chamber and a second chamber, whereby said first and second chambers are separated by said material, and said isotopic gases enter said second chamber through said material;
   c. analysing said isotopic gases in said second chamber, so as to derive a permeation of each of said corresponding target gas through said material, and
   d. conducting a preliminary permeation analysis prior to said mixture formation comprising the steps of filling said first chamber with helium, and calculating a permeation of said helium through said material such that said material is preselected by excluding said material from subsequent analysis if said helium permeation is greater than a determined threshold.

2. The method of claim 1, wherein said step of forming a mixture of isotopic gases comprises:

a. filling said mixing enclosure with at least one isotopic gas,
   b. closing said mixing enclosure,
   c. regulating heavy water vapour in said isotopic gas mixture, and
   d. waiting for said isotopic gas mixture to reach equilibrium.

3. The method of claim 2, wherein said mixing enclosure is filled with an isotopic gas selected from the group consisting of $^{18}O_2$ and $^{17}O_2$ when one of said target gases is $^{16}O_2$.

4. The method of claim 1, wherein said filling step comprises:
   a. creating a vacuum in said first chamber and
   b. opening said mixing enclosure so as to fill said first chamber with said mixture of isotopic gases.

5. The method of claim 1, further comprising the step of regulating a temperature of said permeation enclosure and said mixing enclosure.

6. The method of claim 1, wherein said analysis step comprises determining a presence of said isotopic gases in said second chamber with a gas analyser located in a measurement enclosure in communication with said second chamber.

7. The method of claim 6, further comprising the step of creating a vacuum in said second chamber and said measurement enclosure.

8. The method of claim 1, further comprising the step of recovering said mixture of isotopic gases from said permeation enclosure after said permeation analysis is completed.

9. The method of claim 8, wherein said recovered isotopic gas mixture is transferred to a filter means so as to dry said isotopic gas mixture.

10. The method of claim 9, further comprising trapping said dried gases with a recovery means adapted for recovering said corresponding gas.

11. The method of claim 1, wherein each of said isotopic gases have a mass number different from that of said corresponding target gases.

12. A device for measuring gas permeation through a material comprising:
   a) a permeation enclosure comprising a first chamber and a second chamber separated by said material,
   b) a mixing enclosure for forming a mixture of isotopic gases, said mixing enclosure in communication with said first chamber so as to fill said first chamber with said mixture of isotopic gases, wherein each said isotopic gas corresponds to a different target gas for which permeation through said material is sought,
   c) a gas analysis means in communication with said second chamber for analysis of said isotopic gases having permeated through said material into said second chamber so as to derive a permeation of each said corresponding target gas through said material, and
   d) a gas supply line including first and second ends, said first end in communication with at least one isotopic gas source, and said second end in communication with said first chamber and said mixing enclosure, wherein said supply line is connected to a filter means for drying said gases circulating in said supply line, said filter means includes an inlet and an outlet, said inlet connected to said supply line through a fourth valve and said outlet connected to said supply line through a fifth valve.

13. The device of claim 12, wherein said supply line is connected to said mixing enclosure through a first valve.

14. The device of claim 12, wherein said gas source is connected to a recovery means adapted for recovering said corresponding target gas.

15. The device of claim 14, wherein said recovery means is a cryogenic trap.

16. The device of claim 12, wherein said filter means is a molecular sieve adapted to trap water molecules.

17. The device of claim 12, further comprising a seventh valve inserted at said supply line second end before said first and second valves, so as to isolate said supply line from said mixing enclosure and from said permeation enclosure.

18. The device of claim 12, wherein said supply line is connected to a first pumping means through a ninth valve at said supply line first end, so as to create a vacuum in said supply line.

19. The device of claims 12 or 17, wherein said mixing enclosure is connected to a phase regulation means so as to regulate a phase of a species in said mixing enclosure.

20. The device of claim 19, wherein said phase regulation means is a Peltier effect module regulating a temperature of a saline solution saturated in heavy water.

21. A method for using the permeation measurement device of claim 20 wherein said method comprises the steps of:
    a) placing a film of said material to be measured in said permeation enclosure, and closing all valves of said device,
    b) opening said tenth and eleventh valves and creating a vacuum in said second chamber,
    c) arranging said saline solution within said mixing enclosure and freezing said solution using said Peltier effect module,
    d) opening said first, second, fourth, fifth, sixth, seventh and ninth valves and creating a vacuum in said first chamber, said supply line, said mixing enclosure and said filter means,
    e) closing said second, fourth, fifth and ninth valves,
    f) opening said third valve to fill said mixing enclosure with said isotopic gases from said isotopic gas source,
    g) closing said first valve and recovering said isotopic gas from said supply line using said recovery means,
    h) closing said third, sixth and seventh valves and waiting for said isotopic gas mixture to reach equilibrium,
    i) opening said first and second valves and simultaneously derive a permeation through said material of each of said corresponding target gases.

22. The method of use of claim 21, further comprising the steps of:
    a) closing said sixth valve and opening said third, fourth, fifth and seventh valves, and drying the gases with said filter means, and
    b) recovering said dried gases using said recovery means, and closing said third valve.

23. The device of claim 12, further comprising a temperature regulation means for regulating a temperature of said permeation enclosure and said mixing enclosure.

24. The device of claim 12, further comprising an analyser located in a measurement enclosure, said measurement enclosure having a first end in communication with said second chamber and a second end in communication with a second pumping means.

25. The device of claim 24, wherein said first end is connected to said second chamber through a tenth valve.

26. The device of claim 24, wherein said second pumping means comprises a primary pump and a secondary pump arranged in series.

27. The device of claim 24, wherein said analyser is a mass spectrometer.

28. The device of claim 27, wherein said mass spectrometer is positioned within a gas flow path between said second chamber and said pumps.

29. The device of claim 12, wherein said supply line is connected to said first chamber through a second valve.

30. The device of claim 12, wherein said supply line is connected to said gas source through a third valve.

31. The device of claim 12, wherein said supply line further comprises a sixth valve located between said fourth valve and said fifth valve so as to bypass said supply line.

32. A method for measuring gas permeation through a material comprising the steps of:
    a) forming a mixture of isotopic gases in a mixing enclosure, each of said isotopic gases corresponding to a different target gas for which permeation through said material is sought, each of said isotopic gases having a mass number different from that of said corresponding target gas;
    b) filling a first chamber of a permeation enclosure with said mixture of isotopic gases, said permeation enclosure comprising said first chamber and a second chamber, whereby said first and second chambers are separated by said material, and said isotopic gases enter said second chamber through said material;
    c) analysing said isotopic gases in said second chamber, so as to derive a permeation of each of said corresponding target gas through said material;
    d) filling said first chamber with helium; and
    e) calculating a permeation of said helium through said material such that said material is preselected by excluding said material from subsequent analyses if said helium permeation is greater than a determined threshold.

33. A device for measuring gas permeation through a material comprising:
    a) a permeation enclosure comprising a first chamber and a second chamber separated by said material;
    b) a mixing enclosure for forming a mixture of isotopic gases, said mixing enclosure in communication with said first chamber so as to fill said first chamber with said mixture of isotopic gases, wherein each said isotopic gas corresponds to a different target gas for which permeation through said material is sought;
    c) a gas supply line including first and second ends, said first end in communication with at least one isotopic gas source, said second end in communication with said first chamber and said mixing enclosure; and
    d) a gas analysis means in communication with said second chamber for analysis of said isotopic gases having permeated through said material into said second chamber so as to derive a permeation of each said corresponding target gas through said material;
    wherein said supply line is connected to a filter means for drying said gases circulating in said supply line, said filter means includes an inlet and an outlet, said inlet connected to said supply line through a first valve and said outlet connected to said supply line through a second valve.

34. A device for measuring gas permeation through a material comprising:
    a) a permeation enclosure comprising a first chamber and a second chamber separated by said material,
    b) a mixing enclosure for forming a mixture of isotopic gases, said mixing enclosure in communication with said first chamber so as to fill said first chamber with said mixture of isotopic gases, wherein each said isotopic gas corresponds to a different target gas for which permeation through said material is sought, c) a gas analysis means in communication with said second chamber for analysis of said isotopic gases having permeated through said material into said second chamber so as to derive a permeation of each said corresponding target gas through said material, and wherein said mixing enclosure is connected to a phase regulation means so as to regulate a phase of a species in said mixing enclosure, said phase regulation means is a Peltier effect module regulating a temperature of a saline solution saturated in heavy water.

* * * * *